United States Patent
van Egmond

(10) Patent No.: US 7,388,120 B2
(45) Date of Patent: Jun. 17, 2008

(54) REMOVING CARBON DIOXIDE FROM AN OXYGENATE TO OLEFINS REACTION EFFLUENT

(75) Inventor: Cor F. van Egmond, Pasadena, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 571 days.

(21) Appl. No.: 11/005,427

(22) Filed: Dec. 6, 2004

(65) Prior Publication Data

US 2006/0122449 A1    Jun. 8, 2006

(51) Int. Cl.
*C07C 7/00*    (2006.01)
*C07C 7/12*    (2006.01)

(52) U.S. Cl. .................. 585/809; 585/820; 585/821
(58) Field of Classification Search .......... 585/809, 585/860, 234; 208/81–82
See application file for complete search history.

(56) References Cited

U.S. PATENT DOCUMENTS

| | | | | |
|---|---|---|---|---|
| 3,679,765 A | * | 7/1972 | Houston et al. ............. | 208/255 |
| 3,865,924 A | * | 2/1975 | Gidaspow et al. ........... | 423/230 |
| 4,313,916 A | * | 2/1982 | Jones et al. ................. | 423/226 |
| 5,914,433 A | | 6/1999 | Marker ....................... | 585/313 |
| 6,121,504 A | | 9/2000 | Kuechler et al. ............ | 585/640 |
| 6,235,961 B1 | * | 5/2001 | Kurukchi .................... | 585/854 |
| 6,403,584 B1 | | 6/2002 | de Laszlo et al. ........ | 514/237.2 |
| 6,403,854 B1 | | 6/2002 | Miller et al. | |
| 6,459,009 B1 | | 10/2002 | Miller et al. ................ | 585/809 |
| 2003/0199722 A1 | | 10/2003 | Lattner et al. .............. | 585/809 |
| 2004/0122275 A1 | | 6/2004 | Levin et al. | |
| 2004/0267077 A1 | * | 12/2004 | Ding et al. .................. | 585/809 |

FOREIGN PATENT DOCUMENTS

| WO | WO 03/020672 | 3/2003 |
|---|---|---|
| WO | WO 2005/005347 | 1/2005 |

* cited by examiner

*Primary Examiner*—Walter D. Griffin
*Assistant Examiner*—Frank C Campanell

(57) ABSTRACT

The present invention provides processes for removing $CO_2$ from an effluent stream derived from an oxygenate to olefins reaction system. In one embodiment, the invention comprises contacting the effluent stream with a first $CO_2$ removal medium in a first $CO_2$ removal zone under conditions effective to remove a first portion of the $CO_2$ from the effluent stream and form a first $CO_2$ depleted stream. The first $CO_2$ depleted stream is contacted with a second $CO_2$ removal medium in a second $CO_2$ removal zone under conditions effective to remove a second portion of the $CO_2$ from the first $CO_2$ depleted stream and form a second $CO_2$ depleted stream comprising less than about 0.5 vppm $CO_2$.

54 Claims, 2 Drawing Sheets

REMOVING CARBON DIOXIDE FROM AN OXYGENATE TO OLEFINS REACTION EFFLUENT

FIELD OF THE INVENTION

The present invention relates to $CO_2$ removal. More particularly, the present invention relates to removing $CO_2$ from an effluent stream derived from an oxygenate to olefins reaction system.

BACKGROUND OF THE INVENTION

Light olefins, defined herein as ethylene and propylene, are important commodity petrochemicals useful in a variety of processes for making plastics and other chemical compounds. Ethylene is used to make various polyethylene plastics, and in making other chemicals vinyl chloride, ethylene oxide, ethyl benzene and alcohol. Propylene is used to make various polypropylene plastics, and in making other chemicals such as acrylonitrile and propylene oxide.

In addition to cracking petroleum products, the petrochemical industry has known for some time that oxygenates, especially alcohols, are convertible into light olefins. The preferred conversion process is generally referred to as an oxygenate to olefin (OTO) reaction process. Specifically, in an OTO reaction process, an oxygenate contacts a molecular sieve catalyst composition under conditions effective to convert at least a portion of the oxygenate to light olefins. When methanol is the oxygenate, the process is generally referred to as a methanol to olefin (MTO) reaction process. Methanol is a particularly preferred oxygenate for the synthesis of ethylene and/or propylene.

In a typical OTO reaction system, undesirable byproducts, such as carbon dioxide, may be formed through side reactions. U.S. Pat. No. 6,121,504 discloses a method of making olefin product from an oxygenate feed using molecular sieve catalysts. Water and other unwanted byproducts are removed from the olefin product by contacting with a quench medium. After contacting with the quench medium, a light product fraction is obtained which comprises the desired olefins, but also includes dimethyl ether, methane, CO, $CO_2$, ethane, propane, and other minor components such as water and unreacted oxygenate feedstock.

In order to further process olefins, it is often necessary to reduce or remove undesirable byproducts that are present in the olefin composition. For example, U.S. Pat. No. 5,914,433 discloses a method of making an olefin composition, and a system for removing non-olefin byproducts such as $CO_2$. A dewatered olefin composition is washed with caustic to remove $CO_2$, and the washed olefin composition is dried to reduce water added as a result of the caustic wash.

Published U.S. Patent Application US 2003/0199722 A1 to Lattner et al., the entirety of which is incorporated herein by reference, discloses a method of removing acetaldehyde, $CO_2$ and/or water from an ethylene and/or propylene containing stream. Specifically, acetaldehyde and C4+ olefins are substantially removed from the ethylene and/or propylene containing stream. The stream is then acid gas treated.

Additional processes for removing undesirable components from olefin streams are sought. In particular, processes are sought for removing oxygenated hydrocarbons, particularly $CO_2$, down to the ppm level in olefin product streams without removing significant amounts of olefin.

SUMMARY OF THE INVENTION

The present invention provides a two-stage carbon dioxide removal process and devices for using same, which are ideally suited for removing carbon dioxide from an olefin-containing effluent stream derived from an oxygenate to olefin (OTO) reaction system.

In one embodiment, the invention is to a process for removing $CO_2$ from an effluent stream, wherein the process comprises the steps of: (a) providing the effluent stream, wherein the effluent stream comprises greater than about 100 vppm $CO_2$, optionally greater than about 200 vppm $CO_2$, optionally greater than about 300 vppm $CO_2$, or optionally greater than about 400 vppm $CO_2$; (b) contacting the effluent stream with a first $CO_2$ removal medium in a first $CO_2$ removal zone under conditions effective to remove a first portion of the $CO_2$ from the effluent stream and form a first $CO_2$ depleted stream comprising from about 0.5 to about 200 vppm $CO_2$, optionally from about 0.5 to about 10 vppm $CO_2$, or from about 0.5 to about 1.5 vppm $CO_2$; and (c) contacting the first $CO_2$ depleted stream with a second $CO_2$ removal medium in a second $CO_2$ removal zone under conditions effective to remove a second portion of the $CO_2$ from the first $CO_2$ depleted stream and form a second $CO_2$ depleted stream comprising less than about 0.5 vppm $CO_2$, optionally less than about 0.4 vppm $CO_2$ or less than about 0.32 vppm $CO_2$.

In another embodiment, the invention provides a process for removing $CO_2$ from an effluent stream, wherein the process comprises the steps of: (a) providing the effluent stream, wherein the effluent stream comprises greater than about 100 vppm $CO_2$; (b) contacting the effluent stream with a first $CO_2$ removal medium in a first $CO_2$ removal zone under conditions effective to remove a first portion of the $CO_2$ from the effluent stream and form a first $CO_2$ depleted stream, wherein the first $CO_2$ removal medium has a weight ratio of fresh caustic to spent caustic, on a dry basis, of greater than about 1.5; and (c) contacting the first $CO_2$ depleted stream with a second $CO_2$ removal medium in a second $CO_2$ removal zone under conditions effective to remove a second portion of the $CO_2$ from the first $CO_2$ depleted stream and form a second $CO_2$ depleted stream, wherein the second $CO_2$ removal medium has a weight ratio of fresh caustic to spent caustic, on a dry basis, of less than about 99.0. Preferably, the first $CO_2$ removal medium has a weight ratio of fresh caustic to spent caustic, on a dry basis, of greater than about 1.5 and less than about 4.5, more preferably greater than about 2.3 and less than about 3.7, and most preferably greater than about 2.8 and less than about 3.2. The second $CO_2$ removal medium preferably has a weight ratio of fresh caustic to spent caustic, on a dry basis, of greater than about 1.0 and less than about 99.0, more preferably greater than about 5.0 and less than about 19.0, and most preferably greater than about 8.5 and less than about 9.5.

Optionally, the first $CO_2$ removal medium is the same type of solution as the second $CO_2$ removal medium. The first $CO_2$ removal medium optionally comprises greater than about 60 weight percent fresh caustic, on a dry basis. Optionally, the first $CO_2$ removal medium comprises less than about 40 weight percent spent caustic, on a dry basis. In one embodiment, the first $CO_2$ removal medium comprises greater than about 70 weight percent fresh caustic and less than about 30 weight percent spent caustic, optionally greater than about 74 weight percent fresh caustic and less than about 26 weight percent spent caustic, on a dry basis.

The second $CO_2$ removal medium optionally comprises greater than about 1.0 weight percent spent caustic. Optionally, the second $CO_2$ removal medium comprises less than about 99.0 weight percent fresh caustic. The second $CO_2$ removal medium optionally comprises greater than about 5.0 weight percent spent caustic and less than about 95.0 weight percent fresh caustic, preferably greater than about 8.0 weight percent spent caustic and less than about 92.0 weight percent fresh caustic.

The conditions in the first and second $CO_2$ removal zones may vary widely. In one embodiment, the temperature in the first and second $CO_2$ removal zones ranges from about 38° C. to about 66° C., optionally from about 43° C. to about 54° C. The pressure in the first and second $CO_2$ removal zones optionally ranges from about 1034 kPaa to about 2758 kPaa, optionally from about 1724 kPaa to about 2413 kPaa.

In another embodiment, the invention is to a system for removing carbon dioxide from an effluent stream comprising greater than about 100, 200, 300 or 400 vppm $CO_2$, the system comprising a $CO_2$ removal unit comprising exactly two $CO_2$ removal zones, wherein the $CO_2$ removal unit removes a majority of the $CO_2$ from the effluent stream to form a final $CO_2$ depleted stream comprising less than about 0.5 vppm $CO_2$, preferably less than about 0.4 vppm, less than about 0.32, less than about 0.2, or less than about 0.1 vppm $CO_2$.

Optionally, the $CO_2$ removal unit is in fluid communication with an oxygenate to olefin reactor. For example, the $CO_2$ removal unit optionally receives the effluent stream from a water absorption column, and the water absorption column receives the effluent stream from a quench unit, and the quench unit receives the effluent stream from the oxygenate to olefin reactor.

The $CO_2$ removal unit preferably further comprises a water wash zone.

Optionally, the $CO_2$ removal unit comprises a first $CO_2$ removal zone and a second $CO_2$ removal zone, wherein a first $CO_2$ removal medium is added to the first $CO_2$ removal zone and a second $CO_2$ removal medium is added to the second $CO_2$ removal zone, the first $CO_2$ removal medium having a weight ratio of fresh caustic to spent caustic of greater than about 1.5 and less than about 4.5, on a dry basis, and the second $CO_2$ removal medium having a weight ratio of fresh caustic to spent caustic of greater than about 1.0 and less than about 99.0, on a dry basis. In this embodiment, the first $CO_2$ removal medium optionally has a weight ratio of fresh caustic to spent caustic of greater than about 2.3 and less than about 3.7, preferably greater than about 2.8 and less than about 3.2. The second $CO_2$ removal medium optionally has a weight ratio of fresh caustic to spent caustic of greater than about 5.0 and less than about 19.0, preferably greater than about 8.5 and less than about 9.5.

In another embodiment, the invention is to a $CO_2$ removal unit in fluid communication with an OTO reaction system, the $CO_2$ removal unit comprising exactly two $CO_2$ removal zones. The $CO_2$ removal unit optionally comprises a first caustic wash zone and a second caustic wash zone. The $CO_2$ removal unit preferably comprises a water wash zone.

BRIEF DESCRIPTION OF THE DRAWINGS

This invention will be better understood by reference to the detailed description of the invention when taken together with the attached drawings, wherein.

DETAILED DESCRIPTION OF THE INVENTION

A. Introduction

Figure 1:
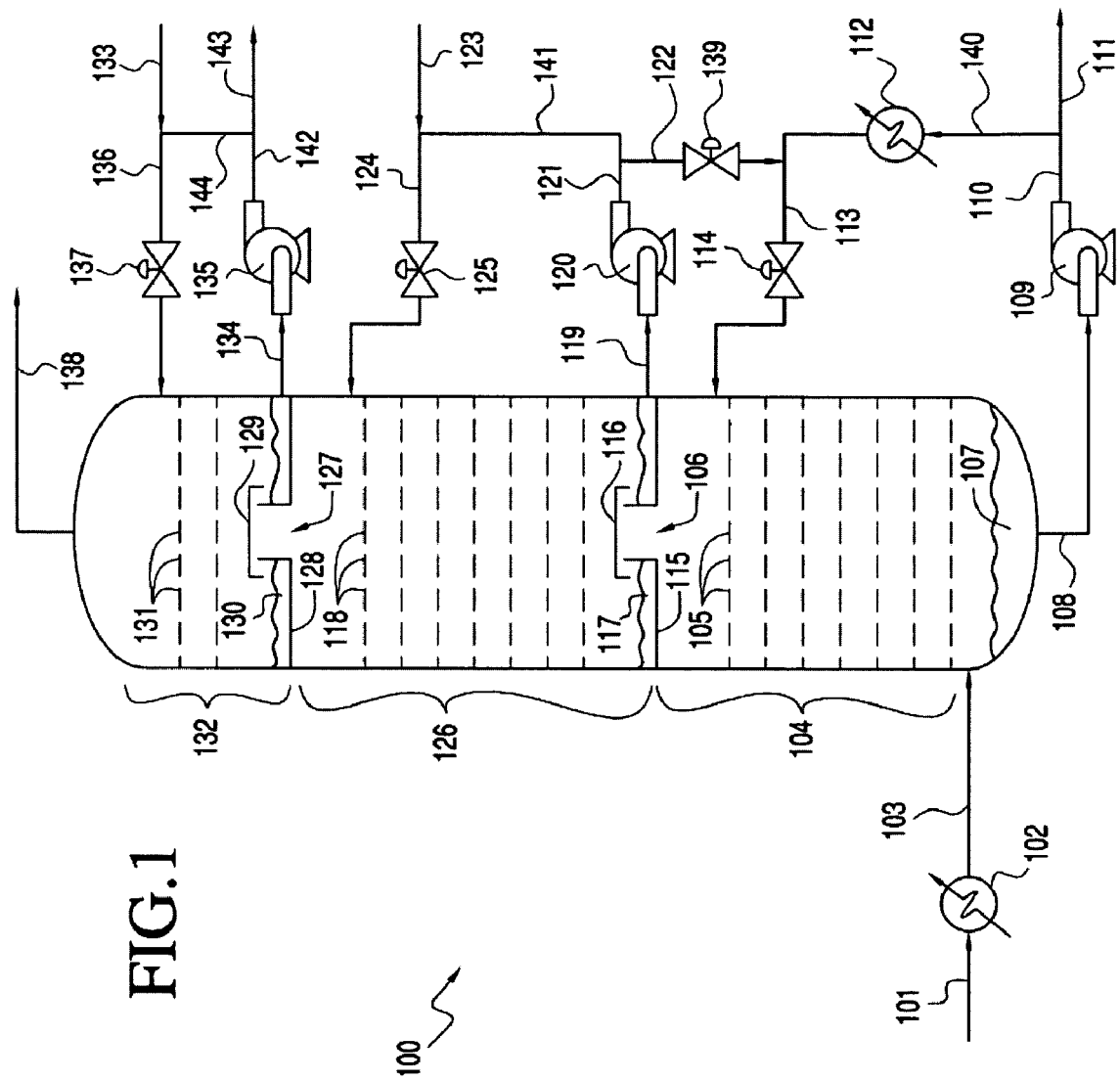
FIG. 1 provides a non-limiting partial cross sectional view of a two stage $CO_2$ removal unit according to one embodiment of the present invention.

The present invention provides processes for removing carbon dioxide from an effluent stream. Preferably, the effluent stream is derived from an oxygenate to olefins (OTO) reaction system, most preferably a methanol to olefins (MTO) reaction system. The inventive process comprises removing the carbon dioxide in two stages.

In a preferred embodiment, the inventive process includes a step of providing an effluent stream, which comprises greater than about 100 vppm $CO_2$. The effluent stream contacts a first $CO_2$ removal medium, preferably comprising caustic, in a first $CO_2$ removal zone under conditions effective to remove a first portion of the $CO_2$ from the effluent stream and form a first $CO_2$ depleted stream comprising less $CO_2$ than was present in the effluent stream, preferably from about 0.5 to about 200 vppm $CO_2$. The first $CO_2$ depleted stream then contacts a second $CO_2$ removal medium in a second $CO_2$ removal zone under conditions effective to remove a second portion of the $CO_2$ from the first $CO_2$ depleted stream and form a second $CO_2$ depleted stream comprising less $CO_2$ than was present in the first $CO_2$ depleted stream, preferably less than about 0.5 vppm $CO_2$. It has been discovered that the novel $CO_2$ removal process of the present invention provides ideal $CO_2$ removal properties for an effluent stream derived from an OTO reaction system.

In another embodiment, the provided effluent stream, which comprises greater than about 100 vppm $CO_2$ contacts a first $CO_2$ removal medium in a first $CO_2$ removal zone under conditions effective to remove a first portion of the $CO_2$ from the effluent stream and form a first $CO_2$ depleted stream. In this embodiment, the first $CO_2$ removal medium has a weight ratio of fresh caustic to spent caustic, on a dry basis, of greater than about 1.5. The first $CO_2$ depleted stream then contacts a second $CO_2$ removal medium in a second $CO_2$ removal zone under conditions effective to remove a second portion of the $CO_2$ from the first $CO_2$ depleted stream and form a second $CO_2$ depleted stream. The second $CO_2$ removal medium has a weight ratio of fresh caustic to spent caustic, on a dry basis, of less than about 99.0.

B. Carbon Dioxide Removal

This invention provides processes for removing carbon dioxide from an effluent stream, preferably an olefin-containing effluent stream derived from an OTO reaction system. In one embodiment, the process comprises providing an effluent stream comprising one or more light olefins and carbon dioxide, and removing a majority of the carbon dioxide present in the effluent stream. The effluent stream can be derived from any conventional source, and can include other components such as, but not limited to, hydrogen, carbon monoxide, methane, ethylene, ethane, propylene, propane, nitrogen, dimethyl ether and C4 compounds.

The invention is particularly beneficial in removing carbon dioxide from an effluent stream derived from an OTO reaction process. In an OTO reaction process an oxygenate such as methanol contacts a catalyst under conditions effective to convert the oxygenate to light olefins and water. Carbon dioxide is a byproduct of the OTO reaction process and may be present in an OTO-derived effluent stream in relatively high concentrations. The presence of carbon dioxide in an olefin-containing effluent stream can cause problems in further processing and separation of the ethylene and propylene from these streams. Additionally, carbon dioxide can poison polyethylene and polypropylene forming catalysts. Polymerization grade ethylene typically require less than 0.3 vppm $CO_2$, and polymerization grade propylene requires less than 1.0 vppm $CO_2$.

Optionally, the effluent stream that is provided for $CO_2$ removal according to the present invention comprises not greater than about 1000 vppm carbon dioxide, preferably not greater than about 500 vppm carbon dioxide, and more preferably not greater than about 100 vppm carbon dioxide, based on the total volume of the effluent stream. Of course, for carbon dioxide to be removed from the effluent stream, some measurable amount must be present. In one embodiment, the provided effluent stream comprises greater than about 100 vppm (0.01 vol. %) carbon dioxide; in another, greater than about 200 vppm (0.02 vol. %) carbon dioxide; in another, greater than about 300 vppm (0.03 vol. %) carbon dioxide; and in yet another, greater than about 400 vppm (0.04 vol. %) carbon dioxide, based on the total weight of the effluent stream.

For purposes of the present specification and the appended claims, the amount of carbon dioxide present in the effluent stream, or in any of the other streams described herein, is determined by gas chromatography as described in analytical standard ASTM D-2505.

In another embodiment, the effluent stream that is provided comprises at least about 25 wt % ethylene. Preferably, the provided effluent stream comprises from about 25 wt % ethylene to about 75 wt % ethylene, more preferably from about 30 wt % to about 60 wt %, and most preferably from about 35 wt % to about 50 wt % propylene, based on the total weight of the effluent stream.

In another embodiment, the effluent stream that is provided also comprises at least about 20 wt % propylene. Preferably, the provided effluent stream comprises from about 20 wt % propylene to about 70 wt % propylene, more preferably from about 25 wt % to about 50 wt % propylene, and most preferably from about 30 wt % to about 40 wt % propylene, based on the total weight of the effluent stream.

Optionally, the provided effluent stream comprises a relatively low concentration of ethane, optionally a lower concentration of ethane than propane. For example, the effluent stream optionally comprises not greater than about 4 wt % ethane, not greater than about 3 wt % ethane, or not greater than about 2 wt % ethane, based on the total weight of the effluent stream.

Optionally, the provided effluent stream comprises a relatively low concentration of propane. For example, the effluent stream optionally comprises not greater than about 5 wt % propane, not greater than about 4 wt % propane, or not greater than about 3 wt % propane, based on the total weight of the effluent stream.

In another embodiment of the invention, the provided effluent stream contains both ethylene and propylene. Desirably, the effluent stream comprises at least about 50 wt % ethylene and propylene. Preferably, the effluent stream comprises from about 50 wt % to about 95 wt % ethylene and propylene, more preferably from about 55 wt % to about 90 wt % ethylene and propylene, and most preferably from about 60 wt % to about 85 wt % ethylene and propylene, based on the total weight of the effluent stream.

Optionally, the provided effluent stream comprises not greater than about 15,000 wppm water. For example, the effluent stream optionally comprises not greater than about 10,000 wppm water, not greater than about 5,000 wppm water, or not greater than about 1,000 wppm water, based on the total weight of the effluent stream.

It is not necessary in this invention that the effluent stream be completely dry. That is, the effluent stream can contain some water. The benefit of the effluent stream containing some amount of water is that additional and/or complex drying equipment will not be needed before separating the carbon dioxide from the effluent stream. Optionally, the effluent stream comprises at least about 10 wppm water, more preferably at least about 100 wppm water, and most preferably at least about 200 wppm water, based on the total weight of the effluent stream.

In another embodiment, the effluent stream that is provided comprises not greater than about 40 wt % C4+ olefins. Preferably, the provided effluent stream comprises not greater than about 30 wt % C4+ olefins, more preferably not greater than about 20 wt % C4+ olefins, based on the total weight of the effluent stream.

As discussed in more detail below, the carbon dioxide removal process according to the present invention is a two stage removal process. In the first stage, the effluent stream contacts a first $CO_2$ removal medium in a first $CO_2$ removal zone under conditions effective to remove a first portion of the $CO_2$ from the effluent stream and form a first $CO_2$ depleted stream. In the second stage, the first $CO_2$ depleted stream contacts a second $CO_2$ removal medium in a second $CO_2$ removal zone under conditions effective to remove a second portion of the $CO_2$ from the first $CO_2$ depleted stream and form a second (final) $CO_2$ depleted stream.

In this embodiment, the first $CO_2$ depleted stream preferably comprises greater than about 0.5 vppm carbon dioxide. Preferably, the first $CO_2$ depleted stream comprises from about 0.5 to about 200 vppm carbon dioxide, preferably, from about 0.5 to about 100 vppm carbon dioxide, more preferably from about 0.5 to about 10 vppm carbon dioxide, and most preferably from about 0.5 to about 1.5 vppm carbon dioxide, based on the total weight of the first $CO_2$ depleted stream.

The second $CO_2$ depleted stream preferably comprises not greater than about 1 vppm carbon dioxide. Preferably, the second $CO_2$ depleted stream comprises not greater than about 0.5 vppm carbon dioxide, more preferably not greater than about 0.4 vppm carbon dioxide, and most preferably not greater than about 0.32 vppm carbon dioxide, based on the total weight of the second $CO_2$ depleted stream.

The second $CO_2$ depleted stream preferably comprises at least a majority of the ethylene and propylene present in the provided effluent stream. Preferably, the second $CO_2$ depleted stream comprises at least about 70 wt % ethylene and propylene, individually or collectively, more preferably at least about 80 wt % ethylene and propylene, individually or collectively, and most preferably at least about 90 wt % ethylene and propylene, individually or collectively, based on the total weight of the $CO_2$ depleted stream.

Following separation of at least a majority (i.e., at least 50%) of the carbon dioxide present in the effluent stream, ethylene and/or propylene containing streams are recovered, which contain at least a majority (i.e., at least 50%) of the ethylene and/or propylene in the provided effluent stream. These ethylene and/or propylene containing streams require little if any further treatment prior to making polymers or other derivative products.

In one embodiment of the invention, ethylene and propylene are recovered and then separated from one another. The streams can be treated, if desired, before or after separation to remove carbon dioxide. It is preferable, however, to acid gas treat (i.e., remove acid gases formed from carbon dioxide such as carbonic acid and sulfuric acid) an effluent stream comprising both ethylene and propylene, and then separate the light olefins in the resulting second $CO_2$ depleted stream into an ethylene stream and a propylene stream. Each derivative stream is then further processed, as is known in the art, to provide final products.

In one embodiment, for example, the ultimately recovered ethylene and/or propylene streams comprise not greater than about 1.0 vppm carbon dioxide. Preferably, the recovered ethylene and/or propylene streams comprise not greater than about 0.7 vppm carbon dioxide, more preferably not greater than about 0.05 vppm carbon dioxide, and most preferably not greater than about 0.03 vppm carbon dioxide, based on the total weight of the recovered ethylene and/or propylene streams.

As indicated above, the carbon dioxide removal process of the present invention includes removing carbon dioxide from the provided effluent stream in two steps. The carbon dioxide preferably is removed by acid gas treating the effluent stream in two steps. Preferably, the effluent stream comprises relatively few hydrocarbon components that cause fouling problems in such acid gas treatment systems.

Solid or liquid acid gas treatment systems can be used in this invention, although liquid acid gas treatment systems are preferred. In either system, the acid gas is removed from the effluent stream in a first fraction by contacting the effluent stream with an acid gas absorbent or adsorbent. Examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred. Thus, the first and/or second $CO_2$ removal medium optionally is selected from the group consisting of amines, potassium carbonate, caustic, alumina, molecular sieves, and membranes, particularly membranes formed of polysulfone, polyimid, polyamide, glassy polymer and cellulose acetate.

As indicated above, the first and second $CO_2$ removal mediums preferably comprise a mixture of fresh and spent caustic. Without limiting the present invention to any specific mechanism, the $CO_2$ removal process of the present invention is believed to occur by the following reactions:

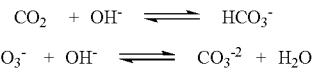

For purposes of the present specification and the appended claims, "caustic," without being modified by the terms "spent" or "fresh," means an alkaline compound in solution, which is effective in removing acid gas from an olefin-containing effluent stream. Examples of such alkaline compounds include sodium hydroxide and potassium hydroxide, preferably sodium hydroxide. Preferably, the caustic comprises one or more of hydroxide ions ($OH^{-1}$), bicarbonate ions ($HCO_3^{-1}$) and/or carbonate ions ($CO_3^{2}$). "Spent caustic" means caustic that has lost at least a portion of its $CO_2$ removal ability, e.g., a solution comprising bicarbonate ions ($HCO_3^{-1}$) and/or carbonate ions ($CO_3^{-2}$). In contrast, "fresh caustic" means caustic that has substantially all of its $CO_2$ removal ability.

The relative amount of spent caustic and fresh caustic present in the first and second $CO_2$ removal mediums is expressed herein in terms of a weight ratio of fresh caustic to spent caustic, on a dry basis. These relative amounts may vary widely between the first and second $CO_2$ removal mediums, as well as between various embodiments of the carbon dioxide removal process of the present invention.

In one embodiment, the first $CO_2$ removal medium comprises greater than about 60 weight percent fresh caustic, preferably greater than about 70 weight percent fresh caustic, and most preferably greater than about 74 weight percent fresh caustic, on a dry basis. In terms of upper range limitations, the first $CO_2$ removal medium optionally comprises less than about weight percent fresh caustic, less than about 80 weight percent fresh caustic or less than about 76 weight percent fresh caustic, on a dry basis. Optionally, the first $CO_2$ removal medium comprises less than about 40 weight percent spent caustic, preferably less than about 30 weight percent spent caustic, and most preferably less than about 26 weight percent spent caustic, on a dry basis. In terms of lower range limitations, the first $CO_2$ removal medium optionally comprises greater than 10 weight percent spent caustic, greater than 20 weight percent spent caustic or greater than 24 weight percent spent caustic, on a dry basis. For an effluent stream derived from an OTO reaction system, the first $CO_2$ removal medium preferably comprises about 75 weight percent fresh caustic and about 25 weight percent spent caustic.

In terms of ratios, the first $CO_2$ removal medium optionally has a weight ratio of fresh caustic to spent caustic, on a dry basis, of greater than about 1.5, more preferably greater than about 2.3, and most preferably greater than about 2.8. In terms of upper range limits, the first $CO_2$ removal medium optionally has a weight ratio of fresh caustic to spent caustic, on a dry basis, of less than about 4.5, preferably less than about 3.7, and most preferably less than about 3.2. It has now been discovered that a weight ratio of fresh caustic to spent caustic, on a dry basis, of about 3.0 in the first $CO_2$ removal medium is particularly preferred for removing carbon dioxide from an effluent stream derived from an OTO reaction system. Unless otherwise indicated, all amounts and ratios of spent and dry caustic specified in the present specification are on a dry basis.

In one embodiment, the second $CO_2$ removal medium comprises greater than about 1.0 weight percent spent caustic, preferably greater than about 5.0 weight percent spent caustic, and most preferably greater than about 8.0 weight percent spent caustic, on a dry basis. In terms of upper range limitations, the second $CO_2$ removal medium optionally comprises less than about 30 weight percent spent caustic, less than about 20 weight percent spent caustic, or less than about 12 weight percent spent caustic, on a dry basis. Optionally, the second $CO_2$ removal medium comprises less than about 99.0 weight percent fresh caustic, preferably less than about 95.0 weight percent fresh caustic, and most preferably less than about 92.0 weight percent fresh caustic, on a dry basis. In terms of lower range limitations, the second $CO_2$ removal medium comprises greater than about 70 weight percent fresh caustic, greater than about 80 weight percent fresh caustic or greater than about 88 weight percent fresh caustic, on a dry basis. For an effluent stream derived from an OTO reaction system, the second $CO_2$ removal medium preferably comprises about 90 weight percent fresh caustic and about 10 weight percent spent caustic.

In terms of ratios, the second $CO_2$ removal medium optionally has a weight ratio of fresh caustic to spent caustic, on a dry basis, of less than about 99.0, more preferably less than about 19.0, and most preferably less than about 9.5. In terms of lower range limitations, the second $CO_2$ removal medium optionally has a weight ratio of fresh caustic to spent caustic, on a dry basis, of greater than about 1.0, more preferably greater than about 5.0, and most preferably greater than about 8.5. It has now been discovered that a weight ratio of fresh caustic to spent caustic, on a dry basis, of about 9.0 in the second $CO_2$ removal medium is particularly preferred for removing carbon dioxide from an effluent stream derived from an OTO reaction system.

In one embodiment, the first $CO_2$ removal medium and the second $CO_2$ removal medium comprise fresh and spent caustic in a water solution, in the relative amounts indicated above. Ideally, either or both the first and second $CO_2$ removal mediums comprise about 80 weight percent water, the balance comprising the weight of the fresh and spent caustic in solution. In terms of ranges, the first and/or second $CO_2$ removal mediums optionally comprise a solution comprising from about 65 to about 95 weight percent water, preferably from about 70 to about 90 weight percent water, and most preferably from about 75 to about 85 weight percent water, based on the total weight of the respective first and/or second $CO_2$ removal mediums.

In one embodiment, the first $CO_2$ removal medium is the same type of solution as the second $CO_2$ removal medium. By "same type," it is meant that the first $CO_2$ removal medium contains the same components as the second $CO_2$ removal medium, although possibly in different amounts. For example, the first and second $CO_2$ removal mediums may comprise both fresh and spent caustic, but in different amounts. Such $CO_2$ removal mediums are considered of the same type. In contrast, if the first $CO_2$ removal medium comprises caustic and the second $CO_2$ removal medium comprises an amine, but no fresh caustic, then these removal mediums would be of different types.

Optionally either or both the first and second $CO_2$ removal mediums comprise an aqueous amine solution. Aqueous amine solutions that are useful in this invention can contain any amine compound or compounds suitable for acid gas absorption. Examples include, but are not limited to, alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations can range from about 0.5 to about 8 moles of amine per liter of aqueous solution.

Piperazine and/or monomethylethanolamine (MMEA) can be added to aqueous amine solutions to enhance their absorption capabilities. These additives can be included in the aqueous solution at a concentration of from about 0.04 to about 2 moles per liter of aqueous solution.

Following acid gas treating, it is desirable to remove additionally entrained material, particularly entrained caustic salts, in the second $CO_2$ depleted stream using a water wash. In a preferred embodiment, this water wash step occurs at the top section of the $CO_2$ removal unit, e.g., in a third zone. It is contemplated that a portion of the water used in the water wash may spill over into the second $CO_2$ removal zone and/or into the first $CO_2$ removal zone causing further dilution of the second and/or first $CO_2$ removal mediums. It is contemplated that this water spill-over may cause the second and/or first $CO_2$ removal mediums to become diluted to about 95 weight percent water, the balance being the spent and/or fresh caustic in solution. Higher dilution levels should be avoided if possible.

Conditions in the first and second $CO_2$ removal zones may vary widely. In one embodiment, the temperature in the first and/or second $CO_2$ removal zones ranges from about 38° C. to about 66° C., preferably from about 43° C. to about 54° C. The pressure in the first and/or second $CO_2$ removal zones optionally ranges from about 1034 kPaa to about 2758 kPaa, preferably from about 1724 kPaa to about 2413 kPaa. It is contemplated, however, that the pressure in the second $CO_2$ removal zone will be slightly less than the pressure in the first $CO_2$ removal zone in order to facilitate the flow of the first $CO_2$ depleted stream to the second $CO_2$ removal zone. Preferably, this pressure differential between the first and second $CO_2$ removal zones will be on the order of from about 6.8 kPaa to about 68 kPaa. A similar pressure differential preferably exists between the second $CO_2$ removal zone and the optional water wash zone.

In another embodiment, the invention is to a $CO_2$ removal unit, preferably a $CO_2$ removal unit that is in fluid communication with an OTO reaction system. The $CO_2$ removal unit comprises exactly two $CO_2$ removal zones. By "exactly two" it is meant that the $CO_2$ removal unit contains precisely two $CO_2$ removal zones, no more and no fewer, although the $CO_2$ removal unit may comprise one or more additional types of zones, e.g., a water wash zone.

The $CO_2$ removal unit optionally comprises a first caustic wash zone and a second caustic wash zone. The $CO_2$ removal unit preferably further comprises a water wash zone. A non-limiting example of this embodiment is illustrated in FIG. 1, which is discussed in more detail below.

FIG. 1 illustrates a two stage $CO_2$ removal unit, generally designated 100, according to one embodiment of the present invention. As shown, the $CO_2$ removal unit 100 generally comprises three zones: a first $CO_2$ removal zone 104, a second $CO_2$ removal zone 126, and a water wash zone 132. Thus, the $CO_2$ is removed from effluent stream 101 in two $CO_2$ removal zones.

In operation, effluent stream 101, which comprises greater than about 100 vppm $CO_2$, is directed to heat exchanger 102 in which the effluent stream 101 is heated to form vaporized effluent stream 103. It is desirable to heat effluent stream 101 in order to improve the flow characteristics of the effluent stream 101 and ensure that the effluent stream 101 is in vapor form prior to its introduction into the $CO_2$ removal unit 100.

Vaporized effluent stream 103 is introduced into first $CO_2$ removal zone 104. Preferably, vaporized effluent stream 103 is introduced into the bottom section of the first $CO_2$ removal zone 104, as shown. Upon entry into first $CO_2$ removal zone 104, the vaporized effluent stream 103 is directed in an upward direction due to a minimal pressure differential between the first $CO_2$ removal zone 104 and the second $CO_2$ removal zone 126. Preferably, first $CO_2$ removal zone 104 includes a plurality of plates 105, as shown, sieves and/or packing. The plates 105, sieves and/or packing in first $CO_2$ removal zone 104 act to increase the surface area of a first $CO_2$ removal medium, which is introduced into the first $CO_2$ removal zone 104 via line 113, in the first $CO_2$ removal zone 104 and thereby improve the contacting between the vaporized effluent stream 103 and the first $CO_2$ removal medium.

As the vaporized effluent stream moves in an upward direction through the first $CO_2$ removal zone 104 and contacts the first $CO_2$ removal medium, a first portion of the $CO_2$ is removed from the vaporized effluent stream to form a first $CO_2$ depleted stream, which preferably comprises from about 0.5 to about 200 vppm $CO_2$. The first $CO_2$ depleted stream is directed through one or more openings 106 in tray 115 (one is shown), which separates the first $CO_2$ removal zone 104 from the second $CO_2$ removal zone 126.

As indicated above, a first $CO_2$ removal medium is introduced into the first $CO_2$ removal zone 104 via line 113. The first $CO_2$ removal medium moves in a downward direction in the first $CO_2$ removal zone 104 due to gravity effects. A portion of the first $CO_2$ removal medium may collect temporarily on the plates 105, sieves and/or packing as the first $CO_2$ removal medium travels in a downward direction. Ultimately, the first $CO_2$ removal medium, which preferably comprises caustic, accumulates in the bottom of the $CO_2$ removal unit 100, as shown by first caustic pool 107.

The caustic in the first caustic pool 107, which comprises a mixture of fresh and spent caustic, preferably is withdrawn from the $CO_2$ removal unit 100 via line 108 and pumped by pump 109 to form pumped stream 110. The caustic in the first caustic pool 107 also may comprise a minor amount of "red oil," defined herein as a mixture of hydrocarbon components and aldol condensate products. It is preferred that the red oil be separated from the aqueous phase prior to recycling of the aqueous phase to the top of the first $CO_2$ removal zone 104 as the first $CO_2$ removal medium. This red oil, however, may form an emulsion with the aqueous phase in the first caustic pool 107 making this separation difficult. Preferably, the emulsion is broken up with the assistance of a liquid/liquid hydrocyclone, not shown. Vortoil-brand liquid/liquid hydrocyclones are particularly preferred. As shown, pumped stream 110 is divided into a waste caustic stream 111 and a first recycle stream 140.

The disposition of the waste caustic stream 111 depends on the amount of sulfur-containing compounds that were present in the effluent stream. If the effluent stream comprises an appreciable amount of sulfur-containing compounds, the waste caustic stream 111 will also contain sulfur-containing compounds. In this case, waste caustic stream 111 preferably is burned in a spent caustic oxidizer, not shown. The effluent stream processed according to the present invention, however, preferably is derived from an OTO reaction system. Unlike an effluent stream derived from a steam cracking system, OTO derived effluent streams do not comprise an appreciable amount the sulfur-containing compounds. Accordingly, if the effluent stream is derived from an OTO reaction system, waste caustic stream 111 will not contain an appreciable amount of sulfur-containing compounds. In this case, waste caustic stream 111 advantageously may be directed to a waste water treatment facility, not shown, without being processed by a spent caustic oxidizer.

The first recycle stream 140 preferably is heated in heat exchanger 112 to improve the viscosity and other fluid flow characteristics thereof. After heating, the first recycle stream 140 is combined with caustic make up stream 122, which preferably contains a greater amount of fresh caustic than the heated first recycle stream 140, to form the first $CO_2$ removal medium that is introduced into the first $CO_2$ removal zone 104 via line 113. The rate at which the caustic make up stream 122 is added to the heated first recycle stream 140 may be controlled by flow control device 139 to ensure that the first $CO_2$ removal medium has a desired weight ratio of fresh caustic to spent caustic. The flow rate of the first $CO_2$ removal medium through line 113 may be controlled with flow control device 114.

As indicated above, the first $CO_2$ depleted stream is directed from the first $CO_2$ removal zone 104 to the second $CO_2$ removal zone 126 through opening 106 in tray 115. Upon entry into second $CO_2$ removal zone 126, the first $CO_2$ depleted stream is directed in an upward direction due to a minimal pressure differential between the second $CO_2$ removal zone 126 and the water wash zone 132. Preferably, second $CO_2$ removal zone 126 includes a plurality of plates 118, as shown, sieves and/or packing. The plates 118, sieves and/or packing in second $CO_2$ removal zone 126 act to increase the surface area of a second $CO_2$ removal medium, which is introduced into the second $CO_2$ removal zone 126 via line 124, in the second $CO_2$ removal zone 126 thereby improving the contacting between the first $CO_2$ depleted stream and the second $CO_2$ removal medium.

As the first $CO_2$ depleted stream moves in an upward direction through the second $CO_2$ removal zone 126 and contacts the second $CO_2$ removal medium, a second portion of the $CO_2$ is removed from the first $CO_2$ depleted stream to form a second $CO_2$ depleted stream, which preferably comprises less than about 0.5 vppm $CO_2$. The second $CO_2$ depleted stream is directed through one or more openings 127 in tray 128 (one is shown), which separates the second $CO_2$ removal zone 126 from the water wash zone 132.

As indicated above, a second $CO_2$ removal medium is introduced into the second $CO_2$ removal zone 126 via line 124. The second $CO_2$ removal medium preferably moves in a downward direction in the second $CO_2$ removal zone 126 due to gravity effects. A portion of the second $CO_2$ removal medium may collect temporarily on the plates 118, sieves and/or packing as the second $CO_2$ removal medium travels in a downward direction. Ultimately, the second $CO_2$ removal medium, which preferably comprises caustic, accumulates on tray 115, as shown by second caustic pool 117. Cap 116 minimizes the downward flow of the second $CO_2$ removal medium through opening 106 and into the first $CO_2$ removal zone 104. It is contemplated, however, that a portion of second caustic pool 117 may overflow into opening 106 and enter the first $CO_2$ removal zone 104.

The caustic in the second caustic pool 117, which comprises a mixture of fresh and spent caustic, preferably is withdrawn from the second $CO_2$ removal zone 126 via line 119 and pumped by pump 120 to form pumped stream 121. As shown, pumped stream 121 is divided into a caustic make up stream 122, discussed above, and a second recycle stream 141. The second recycle stream 141 optionally is heated in a heat exchanger (not shown) to improve the viscosity and other fluid flow characteristics thereof. After the optional heating, the second recycle stream 141 is combined with a fresh caustic stream 123 in order to increase the $CO_2$ removal ability of the second recycle stream 141 and form the second $CO_2$ removal medium that is introduced into the second $CO_2$ removal zone 126 via line 124. The flow rate of the second $CO_2$ removal medium through line 124 may be controlled with flow control device 125.

In a preferred embodiment of the present invention, the flow rate of the fresh caustic 123 that is added to second recycle stream 141 as well as the flow rate of the caustic make up stream 122 are controlled in order to provide desirable compositions in the first and second $CO_2$ removal mediums. For an OTO derived effluent stream, the first $CO_2$ removal medium preferably is maintained at a weight ratio of fresh caustic to spent caustic, on a dry basis, of greater than about 1.5 and less than about 4.5, more preferably greater than 2.3 and less than 3.7, even more preferably greater than 2.8 and less than 3.2 and most preferably about 3.0. The second $CO_2$ removal medium preferably is maintained at a weight ratio of fresh caustic to spent caustic, on a dry basis, of greater than about 1.0 and less than about 99.0, more preferably greater than about 5.0 and less than about 19.0, even more preferably greater than about 8.5 and less than about 9.5, and most preferably about 9.0.

As indicated above, the second $CO_2$ depleted stream is directed from the second $CO_2$ removal zone 126 to the water wash zone 132 via opening 127. The purpose of the water wash zone 132 is to remove any entrained caustic salts from the second $CO_2$ depleted stream. Upon entry into water wash zone 132, the second $CO_2$ depleted stream is directed in an upward direction due to a minimal pressure differential between the water wash zone 132 and the overhead stream 138. Preferably, water wash zone 132 includes a plurality of plates 131, as shown, sieves and/or packing. The plates 132, sieves and/or packing in water wash zone 132 act to increase the surface area of the water, which is introduced into the water wash zone 132 via line 136, in the water wash zone 132 thereby improving the contacting between the second $CO_2$ depleted stream and the water. The water that is introduced into the water wash zone 132 preferably comprises demineralized water and/or boiler feed water.

As the second $CO_2$ depleted stream moves in an upward direction through the water wash zone 132 and contacts water introduced by line 136, entrained caustic salts are removed from the second $CO_2$ depleted stream to form a washed second $CO_2$ depleted stream. The water washing it the water wash zone 132 does not substantially affect the amount of $CO_2$ in the second $CO_2$ depleted stream. Ultimately, the washed second $CO_2$ depleted stream is yielded from the $CO_2$ removal unit 100 via overhead stream 138, which preferably comprises less than about 0.5 vppm $CO_2$.

As indicated above, water is introduced into the water wash zone 132 via line 136. Preferably, the water moves in a downward direction in the water wash zone 132 due to gravity effects. A portion of the water may collect temporarily on the plates 131, sieves and/or packing as the water travels in a downward direction. Ultimately, the water accumulates on tray 128, as shown by water pool 130. Cap 129 minimizes the downward flow of the water through opening 127 and into the second $CO_2$ removal zone 126. It is contemplated, however, that a portion of the water may overflow into opening 127 and enter the second $CO_2$ removal zone 126.

The water in the water pool 130, which includes dissolved caustic salts absorbed from the second $CO_2$ depleted stream, preferably is withdrawn from the water wash zone 132 via line 134 and pumped by pump 135 to form pumped stream 142. As shown, pumped stream 142 is divided into a water recycle stream 144 and a waste water stream 143. The water recycle stream 144 is combined with a fresh water stream 133, which is added to the improve the caustic salt removal ability of the water added to the water wash zone 132 and form the water stream that is introduced into the water wash zone 132 via line 136. The flow rate of the water through line 136 may be controlled with flow control device 137.

In another embodiment, the invention is to a system for removing carbon dioxide from an effluent stream comprising greater than about 100, 200, 300 or 400 vppm $CO_2$. The system preferably implements any of the processes of the present invention, discussed in more detail above. The system comprises a $CO_2$ removal unit having exactly two $CO_2$ removal zones. By "exactly two" it is meant that the $CO_2$ removal unit contains precisely two $CO_2$ removal zones, no more and no fewer, although the $CO_2$ removal unit may comprise other additional types of zones, e.g., a water wash zone. The $CO_2$ removal unit removes a majority of the $CO_2$ from the effluent stream to form a final $CO_2$ depleted stream, e.g., the second $CO_2$ depleted stream, discussed above. The final $CO_2$ depleted stream comprises less than about 0.5 vppm $CO_2$, preferably less than about 0.4 vppm, less than about 0.32, less than about 0.2, or less than about 0.1 vppm $CO_2$.

Preferably, the $CO_2$ removal unit is in fluid communication with an oxygenate to olefin reactor. For example, the $CO_2$ removal unit optionally receives the effluent stream from a water absorption column, and the water absorption column receives the effluent stream from a quench unit, and the quench unit receives the effluent stream from the oxygenate to olefin reactor. This embodiment is discussed in greater detail below with reference to FIG. 2.

As discussed above, the $CO_2$ removal unit in this embodiment preferably comprises a first $CO_2$ removal zone and a second $CO_2$ removal zone. A first $CO_2$ removal medium is added to the first $CO_2$ removal zone and a second $CO_2$ removal medium is added to the second $CO_2$ removal zone. The first $CO_2$ removal medium has a weight ratio of fresh caustic to spent caustic of greater than about 1.5 and less than about 4.5, on a dry basis, and the second $CO_2$ removal medium has a weight ratio of fresh caustic to spent caustic of greater than about 1.0 and less than about 99.0, on a dry basis. In this embodiment, the first $CO_2$ removal medium optionally has a weight ratio of fresh caustic to spent caustic of greater than about 2.3 and less than about 3.7, preferably greater than about 2.8 and less than about 3.2. The second $CO_2$ removal medium optionally has a weight ratio of fresh caustic to spent caustic of greater than about 5.0 and less than about 19.0, preferably greater than about 8.5 and less than about 9.5.

Although the provided effluent stream can be derived from any conventional source that contains carbon dioxide, the invention is particularly well-suited for removing carbon dioxide from an olefin-containing effluent stream derived from an OTO reaction process. In one embodiment of this invention, an effluent stream containing carbon dioxide is obtained by contacting an oxygenate-containing feedstock with a molecular sieve catalyst. OTO reaction processes will now be described in greater detail.

C. The Oxygenate To Olefins Reaction Process

The carbon dioxide removal process of the present invention is ideally suited for removing carbon dioxide from an olefin-containing effluent stream derived from an OTO reaction system, although it is contemplated that the carbon dioxide removal process may be utilized to remove carbon dioxide from an effluent stream derived from other types of reaction systems A non-limiting list of possible reaction systems in which the processes of the present invention can be implemented includes: catalytic cracking, hydroforming, phthalic anhydride, maleic anhydride, Fischer-Tropsch synthesis, vinyl acetate, acrylonitrile, ethylene dichloride, chloromethane, polyethylene, and polypropylene. As used herein, "reaction system" means a system comprising a reactor, optionally a catalyst regenerator, optionally a catalyst cooler and optionally a catalyst stripper. Since the OTO reaction process is preferred, the OTO reaction process will now be described in greater detail.

In a preferred OTO reaction process, a molecular sieve catalyst composition is used to catalyze the conversion of the oxygenate compound(s) to light olefins. Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. Preferably, the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

The feedstock that is directed to an OTO reaction system optionally contains one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and more preferably from 1 to 4 carbon atoms, and most preferably methanol.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more organic compounds containing at least one oxygen atom. In the most preferred embodiment of the process of invention, the oxygenate in the feedstock comprises one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock comprises one or more of methanol, ethanol, DME, diethyl ether or a combination thereof.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In a preferred embodiment, the feedstock, which ideally contains methanol, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as an oxygenate-to-olefins (OTO) reaction process. In an OTO process, typically an oxygenated feedstock, most preferably a methanol- and ethanol-containing feedstock, is converted in the presence of a molecular sieve catalyst composition into one or more olefins, preferably and predominantly, ethylene and/or propylene, referred to herein as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25.

In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system. The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In one embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents fed to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol, DME, or both, is in the range of from about 20 $hr^{-1}$ to about 300 $hr^{-1}$.

The superficial gas velocity (SGV) of the feedstock including diluent and reaction products within the reactor is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. A SGV of from about 15 ft/sec (5 m/s) to about 60 ft/sec (18 m/s) is preferred. See, for example, U.S. patent application Ser. No. 09/708,753, filed Nov. 8, 2000, which is herein incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

The oxygenate to olefin process forms a substantial amount of water as a byproduct. Much of this water can be removed by cooling the olefin stream from the oxygenate reactor to a temperature below the condensation temperature of the water in the stream. Preferably, the temperature of the product stream is cooled to a temperature below the condensation temperature of the oxygenate feed for the oxygenate to olefins process. In certain embodiments, it is desirable to cool the product stream below the condensation temperature of methanol.

A quench column is one type of equipment that is effective in cooling the olefin stream from the olefin to oxygenate reaction process. In a quench column, a quenching fluid is directly contacted with the olefin stream to cool the stream to the desired condensation temperature. Condensation produces a condensed water containing stream, which is also referred to as a heavy bottoms stream. The olefin portion of the olefin product stream remains a vapor, and exits the quench column as an overhead vapor stream. The overhead vapor stream is rich in olefin product, and can also contain some oxygenated byproducts as well as water. One such oxygenated byproduct is carbon dioxide.

In one embodiment, the quenching fluid is a recycle stream of the condensed water containing the heavy bottoms stream of the quench column. This water containing stream is desirably cooled, e.g., by a heat exchanger, and injected back into the quench column. It is preferred in this embodiment to not inject cooling medium from an outside source into the quench column, although it may be desirable to do so in other separation equipment down stream of the quench column.

In one particular embodiment of the invention, the quenched olefin stream is further processed by compression, preferably multi-staged compression. Two, three, four or more stages can be used, with two or three stages being preferred.

Preferably, the olefin stream is compressed to a pressure that is greater than that at which the oxygenate to olefin reaction process is carried out. Preferably, the olefin stream is compressed to a pressure of at least about 30 psia (207 kPaa), more preferably at least about 50 psia (345 kPaa), most preferably at least about 100 psia (689 kPaa). High pressure ranges are particularly preferred, with the upper limit being a practical one based on cost of design and ease of operation. Practical high pressure limits are generally considered to be up to about 5,000 psia (34,450 kPaa), with lower limits of about 1,000 psia (6,895 kPaa), about 750 psia (5171 kPaa), and about 500 psia (3447 kPaa) being increasingly preferred.

The compressed effluent stream then preferably is directed to a water absorption column. In the water absorption column, the compressed effluent stream contacts a water absorbent, preferably comprising methanol, under conditions effective to selectively remove some water and some oxygenates such as acetaldehyde and acetone from the compressed effluent stream. In this embodiment, a weight majority of the ethylene and propylene from the compressed effluent stream is recovered in a first fraction, and a weight majority of the methanol and absorbed oxygenates, e.g., acetaldehyde, are recovered in a second fraction. Typically, the first fraction will be the overhead or side fraction of a distillation column, and the second fraction will be a bottoms fraction or additional side fraction of a distillation column.

In one embodiment of the invention, a majority of the ethylene and propylene in the provided olefin stream will be separated in a first fraction and a majority of the absorbed oxygenates in the provided olefin stream will be separated in a second fraction. Preferably, the first fraction will contain at least about 75% of the ethylene and propylene in the provided olefin stream, more preferably at least about 85%, and most preferably at least about 95%.

The first fraction also will contain a weight majority of the carbon dioxide that was present in the compressed effluent stream. Accordingly, the first fraction, or a portion thereof, preferably is directed to the carbon dioxide removal unit of the present invention, described in detail above, for removal of a weight majority of the carbon dioxide therefrom to form a $CO_2$ depleted stream.

Following carbon dioxide removal, it is desirable to remove additionally entrained material, e.g., entrained caustic salts, in the $CO_2$ depleted stream by contacting the $CO_2$ depleted stream with water in a water wash, which preferably is integrated into the carbon dioxide removal unit, as described above with reference to FIG. 1. This contacting is particularly advantageous when water absorbent, e.g., methanol, from the water absorbent column carries over into the first or overhead fraction.

This invention further includes an optional drying embodiment. In this embodiment, a solid or liquid drying system can be used to remove water and/or additional oxygenated hydrocarbons from the $CO_2$ depleted stream.

In the solid drying system, the ethylene and/or propylene having been separated in a first fraction, and acid gas treated and water washed, is contacted with a solid adsorbent to further remove water and oxygenated hydrocarbon to very low levels. The adsorption process preferably is carried out in one or more fixed beds containing a suitable solid adsorbent.

Adsorption is useful for removing low concentrations of water and oxygenated hydrocarbons, and for removing oxygenated hydrocarbons that may not normally be removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Examples of solid adsorbents for removing water and various polar organic compounds, such as oxygenated hydrocarbons and absorbent liquids, include aluminas, silica, 3 Å (0.3 nm) molecular sieves, 4 Å (0.4 nm) molecular sieves, and alumino-silicates. Beds containing mixtures of these sieves or multiple beds having different adsorbent solids can be used to remove water, as well as a variety of oxygenated hydrocarbons.

One or more adsorption beds can be arranged in series or parallel. In one example of a series arrangement, a first bed is used to remove the smallest and most polar molecules which are the easiest to remove. Subsequent beds for removing larger less polar oxygenated species are next in series. As a specific example of one type of arrangement, water is first selectively removed using a 3 Å (0.3 nm) molecular sieve. This bed is then followed by one or more beds containing one or more less selective adsorbents such as a larger pore molecular sieve, e.g., 13× and/or a high surface area active alumina such as Selexorb CD (Alcoa trade name).

In another embodiment, the first bed is a 3.6 Å (0.36 nm) molecular sieve capable of selectively removing both water and methanol. This bed can then be followed by one or more 13× or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the first fraction. The water absorbent can be any liquid effective in removing water from an olefin stream. Preferably, the water absorbent is the same as that previously described.

Preferably, the olefin from the adsorption beds contains less than about 100 wppm water, more preferably less than about 10 wppm, and most preferably less than 1 wppm. Preferably, less than about 10 wppm oxygenated hydrocarbons are present in the stream leaving the adsorption beds, more preferably less than about 5 wppm, and most preferably less than about 1 wppm.

After drying, the $CO_2$ depleted stream is directed to a separation system for separating the various components contained in the $CO_2$ depleted stream, particularly ethylene and propylene. Such separation systems are well-known and are described, for example, in pending U.S. patent application Ser. Nos. 10/124,859 filed Apr. 18, 2002; Ser. No. 10/125,138 filed Apr. 18, 2002; Ser. No. 10/383,204 filed Mar. 6, 2003; and Ser. No. 10/635,410 filed Aug. 6, 2003, the entireties of which are incorporated herein by reference.

Figure 2:
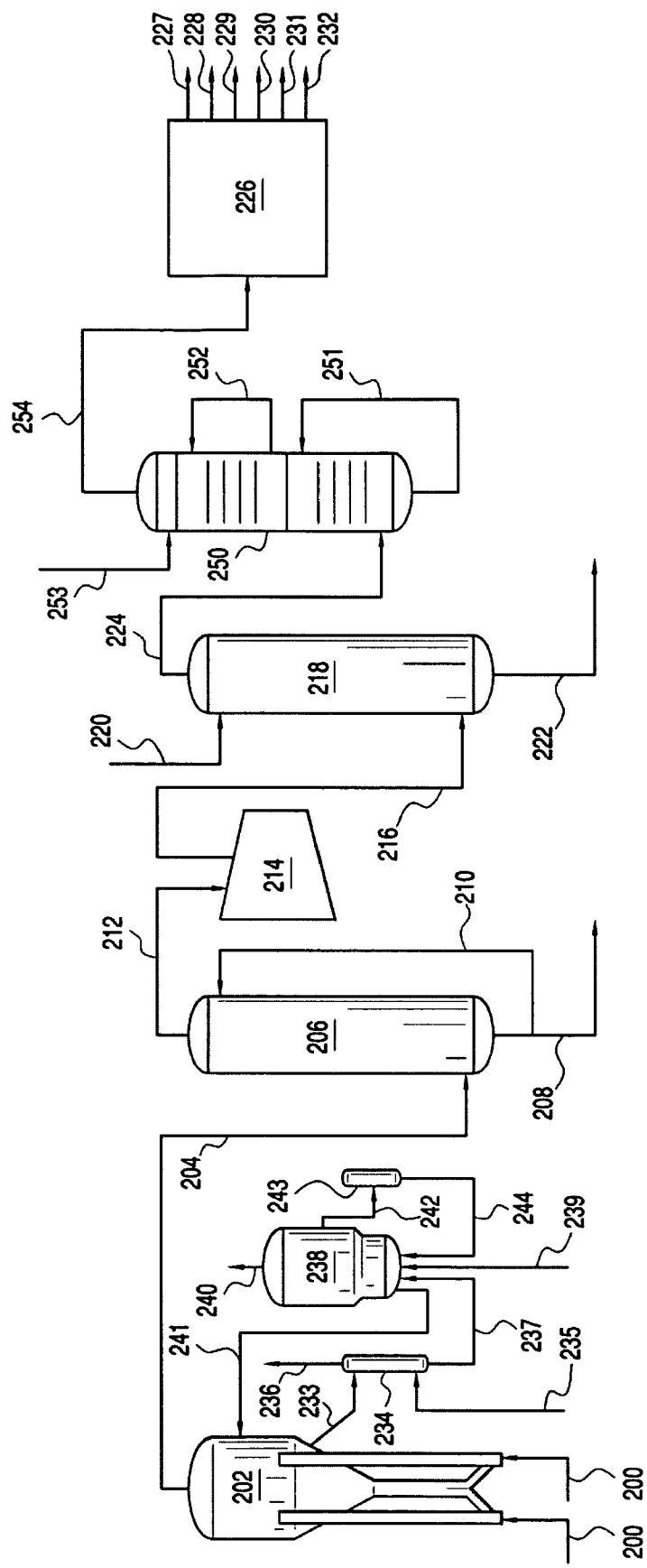
FIG. 2 provides a non-limiting flow diagram illustrating an exemplary non-limiting oxygenate to olefins reaction system, which includes a two stage $CO_2$ removal unit according to one embodiment of the present invention.

FIG. 2 illustrates an OTO reaction system, which includes a $CO_2$ removal unit according to the present invention. In the figure, an oxygenate such as methanol is directed through lines 200 to an OTO fluidized reactor 202 wherein the oxygenate is converted to light olefins and various byproducts which are yielded from the fluidized reactor 202 in an olefin-containing stream in line 204. The olefin-containing stream in line 204 optionally comprises methane, ethylene, ethane, propylene, propane, various oxygenate byproducts including $CO_2$, C4+ olefins, water and hydrocarbon components. The olefin-containing stream in line 204 is directed to a quench unit or quench tower 206 wherein the olefin-containing stream in line 204 is cooled and water and other readily condensable components are condensed.

The condensed components, which comprise water, are withdrawn from the quench tower 206 through a bottoms line 208. A portion of the condensed components are recycled through line 210 back to the top of the quench tower 206. The components in line 210 preferably are cooled in a cooling unit, e.g., heat exchanger (not shown), so as to provide a cooling medium to cool the components in quench tower 206.

An olefin-containing vapor is yielded from the quench tower 206 through overhead stream 212. The olefin-containing vapor is compressed in one or more compressors 214 and the resulting compressed olefin-containing stream is optionally passed through line 216 to a water absorption unit 218. Methanol is preferably used as the water absorbent, and is fed to the top portion of the water absorption unit 218 through line 220. Methanol and entrained water, as well as some oxygenates, are separated as a bottoms stream through line 222. The light olefins are recovered through an overhead effluent stream 224, which comprises $CO_2$ in addition to light olefins. Optionally, the effluent stream 224 is sent to an additional compressor or compressors (not shown) and a heat exchanger (not shown). Ultimately, the effluent stream 224 is directed to CO2 removal unit 250.

As discussed in greater detail above with reference to FIG. 1, the $CO_2$ removal unit 250 of the present invention has two $CO_2$ removal zones. As shown, a first $CO_2$ removal medium 251 is introduced into the first $CO_2$ removal zone in which the first $CO_2$ removal medium 251 contacts the effluent stream 224 under conditions effective to remove a first portion of the $CO_2$ therefrom and form a first $CO_2$ depleted stream, which is directed to the second $CO_2$ removal zone. In the second $CO_2$ removal zone, the first $CO_2$ depleted stream contacts a second $CO_2$ removal medium 252 under conditions effective to remove a second portion of $CO_2$ therefrom and form a second $CO_2$ depleted stream.

In the upper section of the $CO_2$ removal unit 250, the second $CO_2$ depleted stream preferably contacts water from water stream 253 under conditions effective to remove entrained caustic salts therefrom. Ultimately, a washed second $CO_2$ depleted stream 254 is yielded from the $CO_2$ removal unit 250 and directed to a separation system 226, which optionally comprises one or more separation units such as distillation columns, absorption units, and/or adsorption units.

The separation system 226 separates the components contained in the washed second $CO_2$ depleted stream 254. Thus, separation system 226 forms a light ends stream 227, optionally comprising methane, hydrogen and/or carbon monoxide; an ethylene-containing stream 228 comprising mostly ethylene; an ethane-containing stream 229 comprising mostly ethane; a propylene-containing stream 230 comprising mostly propylene; a propane-containing stream 231 comprising mostly propane; and one or more byproduct streams, shown as line 232, comprising one or more of the oxygenate byproducts, provided above, heavy olefins, heavy paraffins, and/or absorption mediums utilized in the separation process. Separation processes that may be utilized to form these streams are well-known and are described, for example, in pending U.S. patent application Ser. Nos. 10/124,859 filed Apr. 18, 2002; Ser. No. 10/125,138 filed Apr. 18, 2002; Ser. No. 10/383,204 filed Mar. 6, 2003; and Ser. No. 10/635,410 filed Aug. 6, 2003, the entireties of which are incorporated herein by reference.

FIG. 2 also illustrates a catalyst regeneration system, which is in fluid communication with fluidized reactor 202. As shown, at least a portion of the catalyst compositions contained in fluidized reactor 202 are withdrawn and transported, preferably in a fluidized manner, in conduit 233 from the fluidized reactor 202 to a catalyst stripper 234. In the catalyst stripper 234, the catalyst compositions contact a stripping medium, e.g., steam and/or nitrogen, under conditions effective to remove interstitial hydrocarbons from the molecular sieve catalyst compositions. As shown, stripping medium is introduced into catalyst stripper 234 through line 235, and the resulting stripped stream 236 is released from catalyst stripper 234. Optionally, all or a portion of stripped stream 236 is directed back to fluidized reactor 202.

During contacting of the oxygenate feedstock with the molecular sieve catalyst composition in the fluidized reactor 202, the molecular sieve catalyst composition may become at least partially deactivated. That is, the molecular sieve catalyst composition becomes at least partially coked. In order to reactivate the molecular sieve catalyst composition, the catalyst composition preferably is directed to a catalyst regenerator 238. As shown, the stripped catalyst composition is transported, preferably in the fluidized manner, from catalyst stripper 234 to catalyst regenerator 238 in conduit 237. Preferably, the stripped catalyst composition is transported in a fluidized manner through conduit 237.

In catalyst regenerator 238, the stripped catalyst composition contacts a regeneration medium, preferably comprising oxygen, under conditions effective (preferably including heating the coked catalyst) to at least partially regenerate the catalyst composition contained therein. As shown, the regeneration medium is introduced into the catalyst regenerator 238 through line 239, and the resulting regenerated catalyst compositions are ultimately transported, preferably in a fluidized manner, from catalyst regenerator 238 back to the fluidized reactor 202 through conduit 241. The gaseous combustion products are released from the catalyst regenerator 238 through flue gas stream 240. In another embodiment, not shown, the regenerated catalyst composition additionally or alternatively is directed, optionally in a fluidized manner, from the catalyst regenerator 238 to one or more of the fluidized reactor 202 and/or the catalyst stripper 234. In one embodiment, not shown, a portion of the catalyst composition in the reaction system is transported directly, e.g., without first passing through the catalyst stripper 234, optionally in a fluidized manner, from the fluidized reactor 202 to the catalyst regenerator 238.

As the catalyst compositions contact the regeneration medium in catalyst regenerator 238, the temperature of the catalyst composition may increase due to the exothermic nature of the regeneration process. As a result, it may be desirable to control the temperature of the catalyst composition by directing at least a portion of the catalyst composition from the catalyst regenerator 238 to a catalyst cooler 243. As shown, the catalyst composition is transported in a fluidized manner from catalyst regenerator 238 to the catalyst cooler 243 through conduit 242. The resulting cooled catalyst composition is transported, preferably in a fluidized manner from catalyst cooler 243 back to the catalyst regenerator 238 through conduit 244. In another embodiment, not shown, the cooled catalyst composition additionally or alternatively is directed, optionally in a fluidized manner, from the catalyst cooler 243 to one or more of the fluidized reactor 202 and/or the catalyst stripper 234.

D. EXAMPLE

In order to provide a better understanding of the present invention, the following non-experimental example is offered. In this example, a hypothetical $H_2S/CO_2$ removal unit (Unit A) specifically designed for removing $H_2S$ and $CO_2$ from an effluent stream derived from a steam cracking system is compared to a $CO_2$ removal unit (Unit B) of the present invention, which is specifically designed for removing $CO_2$ from an effluent stream derived from an OTO reaction system.

Tables 1 and 2, below, indicate that the relatively high concentration of sulfur-containing compounds in the steam cracking derived effluent stream necessitates a three stage $CO_2$ removal process, while the $CO_2$ in the OTO-derived effluent stream can be efficiently removed in two $CO_2$ removal stages even though the OTO derived effluent stream comprises about three times the amount of $CO_2$ than is present in an effluent stream derived from a steam cracking system.

TABLE 1

Removing $H_2S$ and $CO_2$ from an Steam Cracked Effluent Stream in Three $H_2S/CO_2$ Removal Zones

| Section | Stage No. (from bottom) | Percent Spent Caustic* | $H_2S$ in (vppm) | $H_2S$ out (vppm) | $CO_2$ in (vppm) | $CO_2$ out (vppm) | $CO_2$ in $C_2^=$ (vppm) |
|---|---|---|---|---|---|---|---|
| Bottom | 1 | 40 | 800.000 | 256.495 | 150.000 | 150.000 | 475.71 |
| Bottom | 2 | 40 | 256.495 | 82.237 | 150.000 | 150.000 | 475.71 |
| Bottom | 3 | 40 | 82.237 | 26.367 | 150.000 | 150.000 | 475.71 |
| Bottom | 4 | 40 | 26.367 | 8.454 | 150.000 | 121.502 | 385.34 |
| Bottom | 5 | 40 | 8.454 | 2.710 | 121.502 | 98.419 | 312.13 |
| Bottom | 6 | 40 | 2.710 | 0.869 | 98.419 | 79.721 | 252.83 |
| Bottom | 7 | 40 | 0.869 | 0.279 | 79.721 | 64.575 | 204.80 |
| Bottom | 8 | 40 | 0.279 | 0.089 | 64.575 | 52.307 | 165.89 |
| Bottom | 9 | 40 | 0.089 | 0.029 | 52.307 | 42.370 | 134.37 |
| Bottom | 10 | 40 | 0.029 | 0.009 | 42.370 | 34.320 | 108.84 |
| Bottom | 11 | 40 | 0.009 | 0.003 | 34.320 | 27.800 | 88.17 |
| Bottom | 12 | 40 | 0.003 | 0.001 | 27.800 | 22.518 | 71.42 |
| Middle | 1 | 5 | 0.001 | 0.000 | 22.518 | 17.183 | 54.50 |
| Middle | 2 | 5 | 0.000 | 0.000 | 17.183 | 13.112 | 41.59 |
| Middle | 3 | 5 | 0.000 | 0.000 | 13.112 | 10.006 | 31.73 |
| Middle | 4 | 5 | 0.000 | 0.000 | 10.006 | 7.635 | 24.22 |
| Middle | 5 | 5 | 0.000 | 0.000 | 7.635 | 5.827 | 18.48 |
| Middle | 6 | 5 | 0.000 | 0.000 | 5.827 | 4.446 | 14.10 |
| Middle | 7 | 5 | 0.000 | 0.000 | 4.446 | 3.393 | 10.76 |
| Middle | 8 | 5 | 0.000 | 0.000 | 3.393 | 2.589 | 8.21 |
| Middle | 9 | 5 | 0.000 | 0.000 | 2.589 | 1.976 | 6.27 |
| Middle | 10 | 5 | 0.000 | 0.000 | 1.976 | 1.508 | 4.78 |
| Middle | 11 | 5 | 0.000 | 0.000 | 1.508 | 1.150 | 3.65 |
| Middle | 12 | 5 | 0.000 | 0.000 | 1.150 | 0.878 | 2.78 |
| Top | 1 | 0.1 | 0.000 | 0.000 | 0.878 | 0.666 | 2.11 |
| Top | 2 | 0.1 | 0.000 | 0.000 | 0.666 | 0.505 | 1.60 |
| Top | 3 | 0.1 | 0.000 | 0.000 | 0.505 | 0.383 | 1.21 |
| Top | 4 | 0.1 | 0.000 | 0.000 | 0.383 | 0.290 | 0.92 |
| Top | 5 | 0.1 | 0.000 | 0.000 | 0.290 | 0.220 | 0.70 |
| Top | 6 | 0.1 | 0.000 | 0.000 | 0.220 | 0.167 | 0.53 |
| Top | 7 | 0.1 | 0.000 | 0.000 | 0.167 | 0.127 | 0.40 |
| Top | 8 | 0.1 | 0.000 | 0.000 | 0.127 | 0.096 | 0.30 |
| Top | 9 | 0.1 | 0.000 | 0.000 | 0.096 | 0.073 | 0.23 |

*On a dry basis. The remainder being fresh caustic.

TABLE 2

Removing $CO_2$ from an OTO Effluent Stream in Two $CO_2$ Removal Zones

| Section | Stage No. (from bottom) | Percent Spent Caustic* | $H_2S$ in (vppm) | $H_2S$ out (vppm) | $CO_2$ in (vppm) | $CO_2$ out (vppm) | $CO_2$ in $C_2^=$ (vppm) |
|---|---|---|---|---|---|---|---|
| Bottom | 1 | 25 | 0.000 | 0.000 | 450.000 | 297.519 | 526.91 |
| Bottom | 2 | 25 | 0.000 | 0.000 | 297.519 | 196.706 | 348.37 |
| Bottom | 3 | 25 | 0.000 | 0.000 | 196.706 | 130.053 | 230.33 |
| Bottom | 4 | 25 | 0.000 | 0.000 | 130.053 | 85.985 | 152.28 |
| Bottom | 5 | 25 | 0.000 | 0.000 | 85.985 | 56.849 | 100.68 |
| Bottom | 6 | 25 | 0.000 | 0.000 | 56.849 | 37.586 | 66.57 |
| Bottom | 7 | 25 | 0.000 | 0.000 | 37.586 | 24.850 | 44.01 |
| Bottom | 8 | 25 | 0.000 | 0.000 | 24.850 | 16.430 | 29.10 |
| Bottom | 9 | 25 | 0.000 | 0.000 | 16.430 | 10.863 | 19.24 |
| Bottom | 10 | 25 | 0.000 | 0.000 | 10.863 | 7.182 | 12.72 |
| Bottom | 11 | 25 | 0.000 | 0.000 | 7.182 | 4.748 | 8.41 |
| Bottom | 12 | 25 | 0.000 | 0.000 | 4.748 | 3.139 | 5.56 |
| Bottom | 13 | 25 | 0.000 | 0.000 | 3.139 | 2.076 | 3.68 |

TABLE 2-continued

Removing $CO_2$ from an OTO Effluent Stream in Two $CO_2$ Removal Zones

| Section | Stage No. (from bottom) | Percent Spent Caustic* | $H_2S$ in (vppm) | $H_2S$ out (vppm) | $CO_2$ in (vppm) | $CO_2$ out (vppm) | $CO_2$ in $C_2^-$ (vppm) |
|---|---|---|---|---|---|---|---|
| Bottom | 14 | 25 | 0.000 | 0.000 | 2.076 | 1.372 | 2.43 |
| Bottom | 15 | 25 | 0.000 | 0.000 | 1.372 | 0.907 | 1.61 |
| Top | 1 | 10 | 0.000 | 0.000 | 0.907 | 0.616 | 1.09 |
| Top | 2 | 10 | 0.000 | 0.000 | 0.616 | 0.419 | 0.74 |
| Top | 3 | 10 | 0.000 | 0.000 | 0.419 | 0.284 | 0.50 |
| Top | 4 | 10 | 0.000 | 0.000 | 0.284 | 0.193 | 0.34 |
| Top | 5 | 10 | 0.000 | 0.000 | 0.193 | 0.131 | 0.23 |
| Top | 6 | 10 | 0.000 | 0.000 | 0.131 | 0.089 | 0.16 |
| Top | 7 | 10 | 0.000 | 0.000 | 0.089 | 0.061 | 0.11 |
| Top | 8 | 10 | 0.000 | 0.000 | 0.061 | 0.041 | 0.07 |
| Top | 9 | 10 | 0.000 | 0.000 | 0.041 | 0.028 | 0.05 |
| Top | 10 | 10 | 0.000 | 0.000 | 0.028 | 0.019 | 0.03 |
| Top | 11 | 10 | 0.000 | 0.000 | 0.019 | 0.013 | 0.02 |
| Top | 12 | 10 | 0.000 | 0.000 | 0.013 | 0.009 | 0.02 |
| Top | 13 | 10 | 0.000 | 0.000 | 0.009 | 0.006 | 0.01 |
| Top | 14 | 10 | 0.000 | 0.000 | 0.006 | 0.004 | 0.01 |
| Top | 15 | 10 | 0.000 | 0.000 | 0.004 | 0.003 | 0.00 |

*On a dry basis. The remainder being fresh caustic.

As shown in Tables 1 and 2, above, an effluent stream derived from a steam cracking system comprises substantially more $H_2S$ than an effluent stream derived from an OTO reaction system and about three times less $CO_2$ than is found in an OTO derived effluent stream. Thus, a caustic system in a steam cracking system typically is designed for the removal of both $H_2S$ and $CO_2$. To obtain this objective, steam cracking caustic systems typically include caustic towers having at least three $H_2S/CO_2$ removal zones. As reflected in Table 1, the bottom zone is primarily dedicated to removing $H_2S$ from a steam cracking effluent stream as well as to removing a significant amount of $CO_2$ from the effluent stream. The middle and top removal zones are dedicated primarily to removing residual $CO_2$.

Surprisingly and unexpectedly, however, it has now been discovered that although the amount of carbon dioxide in an OTO derived effluent stream is significantly greater (about 3×) than the amount of $CO_2$ that is contained in a steam cracking derived effluent stream, carbon dioxide removal from an OTO derived effluent stream to polymerization specifications can be effectuated in two carbon dioxide removal zones rather than three.

In order to achieve adequate $CO_2$ removal in two zones, however, it is desirable that the first $CO_2$ removal medium comprise more fresh caustic (less spent caustic) than is present in a $H_2S/CO_2$ removal medium that is typically directed to the bottom $H_2S/CO_2$ removal zone of a steam cracking $H_2S/CO_2$ removal system. Without limiting the present invention in any respect, it is believed that this increased amount of fresh caustic is necessary to overcome mass transfer resistance between the $CO_2$ and the aqueous caustic solution. $H_2S$ removal is not as mass transfer limited.

Having now fully described the invention, it will be appreciated by those skilled in the art that the invention may be performed within a wide range of perimeters within what is claimed, without departing from the spirit and scope of the present invention.

I claim:

1. A process for removing $CO_2$ from an effluent stream, wherein the process comprises the steps of:

(a) providing the effluent stream from an oxygenate to olefin process, wherein the effluent stream comprises greater than about 100 vppm CO2;

(b) contacting the effluent stream with a first $CO_2$ removal medium in a first $CO_2$ removal zone under conditions effective to remove a first portion of the $CO_2$ from the effluent stream and form a first $CO_2$ depleted stream comprising from about 0.5 to about 200 vppm $CO_2$, wherein the first $CO_2$ removal medium has a weight ratio of fresh caustic to spent caustic, on a dry basis, of greater than about 1.5 and less than about 4.5; and (c) contacting the first $CO_2$ depleted stream with a second CO2 removal medium in a second $CO_2$ removal zone under conditions effective to remove a second portion of the $CO_2$ from the first $CO_2$ depleted stream and form a second $CO_2$ depleted stream comprising less than about 0.5 vppm $CO_2$.

2. The process of claim 1, wherein the effluent stream comprises greater than about 200 vppm $CO_2$.

3. The process of claim 2, wherein the effluent stream comprises greater than about 300 vppm $CO_2$.

4. The process of claim 3, wherein the effluent stream comprises greater than about 400 vppm $CO_2$.

5. The process of claim 1, wherein the first $CO_2$ depleted stream comprises from about 0.5 to about 10 vppm $CO_2$.

6. The process of claim 2, wherein the first $CO_2$ depleted stream comprises from about 0.5 to about 1.5 vppm CO2.

7. The process of claim 1, wherein the second $CO_2$ depleted stream comprises less than about 0.4 vppm $CO_2$.

8. The process of claim 2, wherein the second $CO_2$ depleted stream comprises less than about 0.32 vppm $CO_2$.

9. The process of claim 1, wherein the first $CO_2$ removal medium is the same type of solution as the second $CO_2$ removal medium.

10. The process of claim 1, wherein the first $CO_2$ removal medium comprises greater than about 60 weight percent fresh caustic, on a dry basis.

11. The process of claim 1, wherein the first $CO_2$ removal medium comprises less than about 40 weight percent spent caustic, on a dry basis.

12. The process of claim 1, wherein the first $CO_2$ removal medium has a weight ratio of fresh caustic to spent caustic, on a dry basis, of greater than about 2.3 and less than about 3.7.

13. The process of claim 12, wherein the first $CO_2$ removal medium has a weight ratio of fresh caustic to spent caustic, on a dry basis, of greater than about 2.8 and less than about 3.2.

14. The process of claim 1, wherein the second $CO_2$ removal medium comprises greater than about 1.0 weight percent spent caustic, on a dry basis.

15. The process of claim 14, wherein the second $CO_2$ removal medium has a weight ratio of fresh caustic to spent caustic, on a dry basis, of greater than about 1.0 and less than about 99.0.

16. The process of claim 15, wherein the second $CO_2$ removal medium has a weight ratio of fresh caustic to spent caustic, on a dry basis, of greater than about 5.0 and less than about 19.0.

17. The process of claim 16, wherein the second $CO_2$ removal medium has a weight ratio of fresh caustic to spent caustic, on a dry basis, of greater than about 8.5 and less than about 9.5.

18. The process of claim 1, wherein the temperature in the first and second $CO_2$ removal zones ranges from about 38° C. to about 66° C.

19. The process of claim 18, wherein the temperature in the first and second $CO_2$ removal zones ranges from about 43° C. to about 54° C.

20. The process of claim 1, wherein the pressure in the first and second $CO_2$ removal zones ranges from about 1034 kPaa to about 2758 kPaa.

21. The process of claim 20, wherein the pressure in the first and second $CO_2$ removal zones ranges from about 1724 kPaa to about 2413 kPaa.

22. A process for removing $CO_2$ from an effluent stream, wherein the process comprises the steps of:
  (a) providing the effluent stream from an oxygenate to olefin process, wherein the effluent stream comprises greater than about 100 vppm CO2;
  (b) contacting the effluent stream with a first $CO_2$ removal medium in a first $CO_2$ removal zone under conditions effective to remove a first portion of the $CO_2$ from the effluent stream and form a first $CO_2$ depleted stream, wherein the first $CO_2$ removal medium has a weight ratio of fresh caustic to spent caustic, on a dry basis, of greater than about 1.5; and
  (c) contacting the first $CO_2$ depleted stream with a second CO2 removal medium in a second $CO_2$ removal zone under conditions effective to remove a second portion of the $CO_2$ from the first $CO_2$ depleted stream and form a second $CO_2$ depleted stream, wherein the second $CO_2$ removal medium has a weight ratio of fresh caustic to spent caustic, on a dry basis, of less than about 99.0.

23. The process of claim 22, wherein the effluent stream comprises greater than about 200 vppm $CO_2$.

24. The process of claim 23, wherein the effluent stream comprises greater than about 300 vppm $CO_2$.

25. The process of claim 24, wherein the effluent stream comprises greater than about 400 vppm $CO_2$.

26. The process of claim 22, wherein the first $CO_2$ depleted stream comprises from about 0.5 to about 200 vppm $CO_2$.

27. The process of claim 26, wherein the first $CO_2$ depleted stream comprises from about 0.5 to about 10 vppm $CO_2$.

28. The process of claim 27, wherein the first $CO_2$ depleted stream comprises from about 0.5 to about 1.5 vppm $CO_2$.

29. The process of claim 22, wherein the second $CO_2$ depleted stream comprises less than about 0.5 vppm CO2.

30. The process of claim 29, wherein the second $CO_2$ depleted stream comprises less than about 0.4 vppm $CO_2$.

31. The process of claim 30, wherein the second $CO_2$ depleted stream comprises less than about 0.32 vppm $CO_2$.

32. The process of claim 22, wherein the first $CO_2$ removal medium is the same type of solution as the second $CO_2$ removal medium.

33. The process of claim 22, wherein the first $CO_2$ removal medium has a weight ratio, on a dry basis, of fresh caustic to spent caustic of greater than about 1.5 and less than about 4.5.

34. The process of claim 33, wherein the first $CO_2$ removal medium has a weight ratio, on a dry basis, of fresh caustic to spent caustic of greater than about 2.3 and less than about 3.7.

35. The process of claim 34, wherein the first $CO_2$ removal medium has a weight ratio, on a dry basis, of fresh caustic to spent caustic of greater than about 2.8 and less than about 3.2.

36. The process of claim 22, wherein the second $CO_2$ removal medium has a weight ratio, on a dry basis, of fresh caustic to spent caustic of greater than about 1.0 and less than about 99.0.

37. The process of claim 36, wherein the second $CO_2$ removal medium has a weight ratio, on a dry basis, of fresh caustic to spent caustic of greater than about 5.0 and less than about 19.0.

38. The process of claim 37, wherein the second $CO_2$ removal medium has a weight ratio, on a dry basis, of fresh caustic to spent caustic of greater than about 8.5 and less than about 9.5.

39. The process of claim 22, wherein the temperature in the first and second $CO_2$ removal zones ranges from about 38° C. to about 66° C.

40. The process of claim 39, wherein the temperature in the first and second $CO_2$ removal zones ranges from about 43° C. to about 54° C.

41. The process of claim 22, wherein the pressure in the first and second $CO_2$ removal zones ranges from about 1034 kPaa to about 2758 kPaa.

42. The process of claim 41, wherein the pressure in the first and second $CO_2$ removal zones ranges from about 1724 kPaa to about 2413 kPaa.

43. A system for removing carbon dioxide from an effluent stream from an oxygenate to olefin process comprising greater than about 100 vppm CO2, the system comprising a $CO_2$ removal unit in fluid communication with an oxygenate to olefin reactor comprising exactly two CO2 removal zones, wherein the $CO_2$ removal unit removes a majority of the $CO_2$ from the effluent stream to form a final $CO_2$ depleted stream comprising less than about 0.5 vppm CO2, wherein the $CO_2$ removal unit comprises a first $CO_2$ removal zone and a second $CO_2$ removal zone, wherein a first $CO_2$ removal medium is added to the first $CO_2$ removal zone and a second $CO_2$ removal medium is added to the second $CO_2$ removal zone, the first $CO_2$ removal medium having a weight ratio of fresh caustic to spent caustic of greater than about 1.5 and less than about 4.5, on a dry basis, and the second $CO_2$ removal medium having a weight ratio of fresh caustic to spent caustic of greater than about 1.0 and less than about 99.0, on a dry basis.

44. The system of claim 43, wherein the $CO_2$ removal unit receives the effluent stream from a water absorption column, and the water absorption column receives the effluent stream from a quench unit, and the quench unit receives the effluent stream from the oxygenate to olefin reactor.

45. The system of claim 43, wherein the $CO_2$ removal unit further comprises a water wash zone.

46. The system of claim 43, wherein the effluent stream comprises greater than about 200 vppm $CO_2$.

47. The system of claim 46, wherein the effluent stream comprises greater than about 300 vppm $CO_2$.

48. The system of claim 47, wherein the effluent stream comprises greater than about 400 vppm $CO_2$.

49. The system of claim 43, wherein the first $CO_2$ removal medium has a weight ratio of fresh caustic to spent caustic of greater than about 2.3 and less than about 3.7.

50. The system of claim 49, wherein the first $CO_2$ removal medium has a weight ratio of fresh caustic to spent caustic of greater than about 2.8 and less than about 3.2.

51. The system of claim 43, wherein the second $CO_2$ removal medium has a weight ratio of fresh caustic to spent caustic of greater than about 5.0 and less than about 19.0.

52. The system of claim 51, wherein the second $CO_2$ removal medium has a weight ratio of fresh caustic to spent caustic of greater than about 8.5 and less than about 9.5.

53. The system of claim 43, wherein the final $CO_2$ depleted stream comprises less than about 0.4 vppm $CO_2$.

54. The system of claim 53, wherein the final $CO_2$ depleted stream comprises less than about 0.32 vppm $CO_2$.

* * * * *